United States Patent [19]

Elias et al.

[11] 4,233,345
[45] Nov. 11, 1980

[54] THIN-SKIN STABILIZATION OF PADS OF FLUFFED PULP

[75] Inventors: Robert T. Elias, Downers Grove; Dennis C. Holtman, Orland Park, both of Ill.

[73] Assignee: Johnson & Johnson Baby Products Company, New Brunswick, N.J.

[21] Appl. No.: 32,181

[22] Filed: Apr. 23, 1979

Related U.S. Application Data

[63] Continuation-in-part of Ser. No. 943,277, Sep. 18, 1978, abandoned.

[51] Int. Cl.² ........................ B05D 3/00; B05D 3/12
[52] U.S. Cl. ................................. 427/325; 128/287; 128/290 R; 427/326; 427/391; 427/393
[58] Field of Search ................... 128/287, 290 R; 427/391, 393, 325, 326

[56] References Cited

U.S. PATENT DOCUMENTS

| | | | |
|---|---|---|---|
| 3,017,304 | 1/1962 | Burgeni | 427/391 X |
| 3,612,055 | 10/1971 | Mesck et al. | 128/287 |
| 3,706,595 | 12/1972 | Drelich et al. | 260/29.6 NR |
| 3,849,173 | 11/1974 | Drelich et al. | 260/29.6 MM |

*Primary Examiner*—Michael R. Lusignan
*Attorney, Agent, or Firm*—Martha A. Michaels

[57] ABSTRACT

A method is provided for the stabilization of a high loft, low density, air-laid pad of short length fibers by the formation of a thin, reinforcing layer on a surface thereof. The film is formed by first pretreating a surface of the pad with a light spray (at a level not higher than about 15 cc per sq. meter of the pad) of a solution of a coagulating material for a resin dispersion, and then applying the resin dispersion to the pretreated surface and limiting its penetration into the pad by instant coagulation thereof.

9 Claims, No Drawings

THIN-SKIN STABILIZATION OF PADS OF FLUFFED PULP

The present application is a Continuation-in-Part of co-pending application U.S. Ser. No. 943,277 filed Sept. 18, 1978, abandoned.

BACKGROUND OF THE INVENTION

Air laid pads of comminuted wood pulp, or other short length cellulosic fibers such as cotton linters, are often used as constituents of absorbent structures, such as diapers and sanitary napkins. Such pads can also serve in structures where cushioning, alone, is the objective and water absorbency may be neither needed nor desired.

The air laying of dry fibers has a substantial advantage over wet laying for the foregoing purposes because dry fibers are relatively stiff and do not sag against each other as wet fibers do; and the dry fibers therefore produce a bulkier, or higher loft structure. A bulkier structure has a greater potential absorbent capacity for liquids and also a greater cushioning ability.

On the other hand, an air laid mass of fibers is essentially composed of a number of completely loose fibers, free except for friction, to move past and away from each other. There is little, if any, of the "natural" or hydrogen bonding among the fibers which develops when wet cellulose fibers are dried in contact with each other, the bonding which is the basis of papermaking.

An air laid pad is therefore easily broken up when subjected to handling such as would occur if the pad were utilized as an element in a diaper. The pad breaks in some places and bunches up in others. Where it breaks, it forms a gap which impedes the desired spreading of absorbed liquid from one area to another. Where is bunches up, it can be uncomfortable to the wearer.

To minimize the tendency of air laid pads to break up and for portions thereof to shift relative to each other, it is common to enclose an air laid pad in creped paper when the air laid pad is used as the absorbent element in a diaper. This is costly because creped paper is a comparatively expensive material, a separately made finished product in itself, because the creped paper, being a wet laid product, is relatively dense and therefore has little liquid holding capacity per unit weight of fiber, and because of the process complexity involved in the infeed of the creped paper and the wrapping of the air laid pads therewith.

An improved reinforcement system for air laid pads, disclosed in Burgeni U.S. Pat. No. 3,017,304, avoids the use of crepe paper wrapping by providing a densified skin on the pad which is integral therewith. The densified skin is prepared by the application of a water spray to one surface of the pad, compressing the pad, and then permitting the pad to dry. Under the force of compression, the entire pad becomes somewhat more dense, but the densification is substantially more pronounced where the fibers have been dampened and are therefore more limp. Upon drying, the dampened fibers develop hydrogen bonding and become a paper-like layer which blends gradually into the main mass of the pad with no sharp line of demarcation. There are many fibers in the structure which are immobilized at one end in the paper-like layer through hydrogen bonding and which at the other end, though relatively free are still restrained to a degree and capable of restraining other fibers which happen to be entangled among them.

Experience has shown that such densified, paper-like skins effectively prevent breaking and bunching in an air laid pad, particularly when the skin is protected from surface abrasion by a cover of some kind, such as a diaper facing. In addition, the densified skin can be anchored, as in a diaper, to a plastic skin or a fabric, which serves as further reinforcement.

The strength of the paper-like skin is a function of its average density and thickness. In other words, it is dependent on how much of the pad volume has been sacrificed for production of the skin. Furthermore, compression of the pad in the formation of the skin reduces the volume of the pad beyond the limit of the spray penetration and thus reduces its liquid holding capacity.

In an entirely different system used for manufacture of print bonded non-wovens, Drelich and Drelich et al. U.S. Pat. Nos. 3,706,595; 3,720,562; 3,769,067; 3,821,146; 3,849,173; 3,857,728; 3,873,486; and 3,889,024 teach the reinforcement of fibrous structures with resinous systems whose migration in the fibrous structure is limited by the conversion of a relatively free-flowing resinous dispersion to a nonflowing coagulated layer. Among the resinous systems disclosed in the Drelich and Drelich et al. patents are systems which are stable dispersions at certain concentrations but which become unstable and coagulate when diluted. To achieve dilution rapidly, the fibrous structures are pretreated with large amounts of water and this water immediately dilutes the stable dispersion when the latter is applied to a surface of the fibrous structure. Such prewetting makes the fibers limp throughout the pad and tends to compress the pad and reduce its loft.

SUMMARY OF THE INVENTION

In accordance with the present invention, a high loft, low density air laid pad of short length fibers is reinforced with substantially no loss in loft by a method for stabilizing a high loft, low density air laid pad of short length fibers which comprises pretreating a surface of said pad with a light spray, at a level not higher than about 15 cc per sq. meter and not higher than about 5% of the weight per unit area of said pad, of a solution of a coagulating material for a resin dispersion while maintaining substantially the entire interior of said pad dry, and applying said resin dispersion to said pretreated surface thereby causing coagulation of said dispersion and limiting its penetration to the interior of said pad, whereby a reinforcing layer is obtained on said pad while maintaining substantially its original high loft. Preferably, the light spray is at a level from about 2 to about 10 cc per sq. meter and not higher than about 3% of the weight per unit area of said pad.

DETAILED DESCRIPTION OF THE INVENTION

The coagulating system comprising the resin dispersion and the coagulating material therefor may be selected from among a number of known coagulating systems capable of producing a relatively stiff gel by the reaction of a low viscosity liquid with a small quantity of another material.

One suitable coagulating system comprises a 5% by weight suspension of unneutralized Carbopol #940 (cross-linked polyacrylic acid polymer) as the resin dispersion and aqueous sodium hydroxide as the coagulating material therefor. It takes only a small volume of a strong sodium hydroxide solution to neutralize and gel the Carbopol; and pretreatment of a pad surface with even a light spray of such a sodium hydroxide solution is sufficient to immediately gel a Carbopol suspension thereafter applied to surface and to prevent the suspension from flowing into the pad beyond a thin skin formed at the surface.

As the moisture dissipates, or is removed by drying, the gel suspension breaks up leaving very little residue. Apparently the thin skin formed at the surface results from a collapsing of the fiber system on the surface and hydrogen bonding to form a thin densified layer of fibers otherwise identified as a skin. The thin skin reinforces the pad while the interior of the pad, having never been wetted, nor compressed to form a skin, retains substantially all of its original loft and bulk and substantially all of its original absorptive capacity.

The pads on which the method of this invention is employed are air laid pads made exclusively, or substantially exclusively, of short fibers measuring less than about one-half centimeter in length. The invention is particularly applicable to the reinforcement of air laid pads made of short cellulosic fibers, such as those obtained from wood pulp or cotton linters. Typically, the air laid pads have densities from about 0.05 to about 0.20 g/cc and weights from about 50–300 g/m².

Air laid pads are made by methods known in the art which involve creating an air-borne stream of individualized short fibers and impinging the stream onto a porous surface which permits the air to pass through while retaining and supporting the fibers as a web. When the web is removed from the porous surface, the surface of the web which has been in contact with the porous surface is usually the flatter and smoother surface; and it is this surface which is preferably treated in accordance with this invention.

EXAMPLE

An air laid web made of wood pulp fibers and having a weight of 265 g/sq. meter is cut into pads measuring 26.7×36.8 cm with each pad weighing about 26 grams. The smooth side of one of the pads (which had been in contact with the screen on which the web was formed) is sprayed lightly (at the rate of about 5 cc per sq. meter) with a 5 wt.% solution of sodium hydroxide.

The light spray remains primarily on the surface to which it is applied and substantially all of the interior of the pad remains dry.

The same surface of the pad is then sprayed with a 1% suspension of unneutralized Carbopol #940 (a cross-linked acrylic acid polymer having an equivalent weight of 76 per free acid hydrogen ion and an average molecular weight of about 4,000,000) at the rate of about 45 cc per sq. meter. The Carbopol suspension is a free flowing liquid as applied, but sets up as a stiff gel upon contact with the previously sprayed sodium hydroxide to prevent penetration of the Carbopol spray into the interior of the pad.

The moisture then dissipates or the pad is dried in moderate heat (about 90° C.) resulting in the formation of a thin skin which stabilizes the pad without substantially reducing its original bulk and loft and without substantially reducing its original absorptive capacity.

The thus stabilized pad is assembled with a fibrous facing layer on the side opposite the dried gel layer and with a water-impervious plastic film layer adjacent the dried gel layer and adhered to the dried gel layer by parallel glue lines, spaced about 17 mm apart. The fibrous facing layer and the water-impervious plastic film layer are co-extensive and somewhat larger in dimension than the stabilized pad, being attached to each other by glue lines in the marginal areas in the manner of Mesek et al. U.S. Pat. No. 3,612,055. The loosely assembled portion of the pad of the diaper of this invention, never having been subjected to high compression or substantial wetting, is of higher loft and greater absorptive capacity than the comparable portions of the pads of prior art diapers at comparable pad weights.

The pretreatment of the cellulosic short fibers at the surface of the pad with a light spray of a 5% sodium hydroxide solution results in some mercerization of the fibers. Such mercerization produces an additional advantage in that it enhances the absorptivity of the fibers.

For purposes of illustration, the formation of a thin skin on a fibrous pad has been described with respect to a system utilizing a cross-linked acrylic acid polymer resin and coagulating it by raising its pH. It will be understood, however, by those skilled in the art that other systems capable of coagulating a resin without a large volume of water may also be used.

It is known, for example, that aqueous polyvinyl alcohol dispersions may be coagulated by contact with aqueous borax solutions. The pretreatment of a pad surface with a light spray of a borax solution followed by the application of a heavier spray of a polyvinyl alcohol dispersion will form a thin coagulated film which will prevent further penetration of the latter dispersion to the interior of the pad.

Generally an increase in pH is obtained by pretreating a fibrous pad with a dilute alkaline solution, such as a solution of ammonium hydroxide, sodium hydroxide, potassium hydroxide, lithium hydroxide, or sodium carbonate. When this system is used in the instant invention, the increase in pH is obtained by pretreatment with a more concentrated alkaline material, such as a 5% sodium hydroxide solution, so that a relatively light spray will suffice to achieve the desired increase in pH.

It will be readily apparent to those skilled in the art that numerous variations, modifications and extensions of the principles disclosed herein may be made without departing from the spirit and scope of this invention.

We claim:

1. A method for stabilizing a high loft, low density air laid pad of short length fibers which comprises pretreating a surface of said pad with a light spray, at a level not higher than about 15 cc per sq. meter and not higher than about 5% of the weight per unit area of said pad of a solution of a coagulating material for a resin dispersion while maintaining substantially the entire interior of said pad dry, applying said resin dispersion to said pretreated surface thereby causing coagulation of said dispersion and limiting its penetration to the interior of said pad whereby a reinforcing layer is obtained on said pad while maintaining substantially its original high loft and absorptive capacity.

2. The method of claim 1 wherein said light spray is at a level between about 2 and about 10 cc per sq. meter and not higher than about 3% of the weight per unit area of said pad.

3. The method of claim 1 wherein said pad is composed substantially of cellulosic fibers.

4. The method of claim 3 wherein said pad is composed substantially of wood pulp fibers.

5. The method of claim 1 wherein said pad has a density from about 0.05 to about 0.20 g/cc.

6. The method of claim 1 wherein said pad is dried after application of said resin binder dispersion.

7. The method of claim 1 wherein said resin dispersion comprises a dispersion of a cross-linked acrylic acid polymer and said coagulating material comprises an aqueous solution of an alkali metal hydroxide.

8. The method of claim 7 wherein said acrylic acid polymer has an equivalent weight of 76 per free acid hydrogen ion and an average molecular weight of about 4,000,000 wherein said dispersion is applied to said pad at a rate of about 45 cc per sq. meter, wherein said coagulating material is applied at a rate of about 5 cc per sq. meter and comprises a 5 wt.% solution of sodium hydroxide.

9. A method for stabilizing a high loft, low density air laid pad, composed substantially of short length wood pulp fibers and having a density from about 0.05 to about 0.20 g/cc, which comprises pretreating a surface of said pad with a light spray, at a level from about 2 to about 10 cc sq. meter and not higher than about 3% of the weight per unit area of said pad of a solution of sodium hydroxide while maintaining substantially the entire interior of said pad dry, applying to said pretreated surface an aqueous dispersion of a cross-linked acrylic acid polymer having an equivalent weight of 76 per free acid hydrogen and an average molecular weight of about 4,000,000 thereby causing coagulation of said dispersion and limiting its penetration to the interior of said pad, and thereafter drying said pad whereby a reinforcing layer is obtained on said pad while maintaining substantially its original high loft and absorptive capacity.

* * * * *